United States Patent [19]

Landis

[11] Patent Number: 5,567,345

[45] Date of Patent: Oct. 22, 1996

[54] LOWER VISCOSITY TELOMER OIL

[75] Inventor: Phillip S. Landis, Alexandria, Va.

[73] Assignee: International Lubricants, Inc., Seattle, Wash.

[21] Appl. No.: 380,127

[22] Filed: Jan. 30, 1995

Related U.S. Application Data

[63] Continuation-in-part of Ser. No. 108,477, Aug. 18, 1993, Pat. No. 5,454,965.

[51] Int. Cl.[6] .......................... C10M 129/74; C07C 69/74
[52] U.S. Cl. ........................ 508/486; 554/121; 554/122
[58] Field of Search ................................. 252/57; 560/127

[56] References Cited

U.S. PATENT DOCUMENTS 5,229,023  7/1993  Landis .
5,413,726  5/1995  Landis .

Primary Examiner—Jerry D. Johnson
Attorney, Agent, or Firm—Jeffrey B. Oster

[57] ABSTRACT

There is disclosed a lower range viscosity telomer oil with an acid number of less than 20 and a viscosity range of from 5000 sus to 12,000 sus at 40° C. The lower range viscosity telomer oil product of claim 1 further comprises no more than 4% polyunsaturated fatty acids and a plurality of aliphatic rings, wherein the telomer vegetable oil is made from about 5% to about 15% of a conjugated triglyceride oil, wherein the conjugated triglyceride oil has at least 50% of fatty acids having at least two conjugated double bonds, and from about 85% to about 95% of an unconjugated unsaturated vegetable oil, wherein the unconjugated unsaturated vegetable oil has from about 10% to about 75% of its fatty acids being polyunsaturated and having from about 16 to about 26 carbon atom chain length (unbranched).

15 Claims, 4 Drawing Sheets

LOWER VISCOSITY TELOMER OIL

CROSS REFERENCE TO RELATED APPLICATION

This patent application is a continuation-in-part patent application from U.S. patent application Ser. No. 08/108,477 filed 18 Aug. 1993 now U.S. Pat. No. 5,454,965.

TECHNICAL FIELD OF THE INVENTION

The present invention provides lubricant compositions and lubricant ingredients comprising an improved lower viscosity range telomer oil product having lower acid numbers to improve the oxidation anticorrosion properties of formulations and a lighter color. Moreover, this invention provides an improved stability telomer oil product that does not increase in viscosity.

BACKGROUND OF THE INVENTION

The field of lubricant additives has seen a wide variety of materials used to reduce friction and wear between moving parts. Lubricants are composed principally of a base stock and a lubricant additive. The lubricant additive provides the antifriction and antiwear characteristics to the lubricant. The base stock imparts improved viscosity and thermal/oxidative stability, which can be improved by the addition of various additives. One significant advance in the field was the invention of a material called a "telomer". The telomer invention is described in U.S. Pat. No. 5,229,023, the disclosure of which is incorporated by reference herein.

Briefly, a telomer is a highly viscous polymerized triglyceride oil, principally derived from a seed oil, that has thermal oxidative stability and viscosity improvement characteristics that makes the telomer an essential component or ingredient of a large variety of lubricant formulations. The process to synthesize telomers begins with an unsaturated triglyceride oil and heats the oil in a non-oxidizing atmosphere with a trace water catalyst to lower the iodine number such that no more than 4% of the fatty acid chains of the telomer vegetable oil are polyunsaturated.

An improvement to the telomer oil was made by adding from 20% to 70% of a conjugated triglyceride oil to allow for much thicker telomer oils (i.e., higher viscosity) to be made at lower processing temperatures and times. The improvement was described in U.S. patent application Ser. No. 08/108,477 filed: 18 Aug. 1993, the disclosure of which is incorporated by reference herein. However, lower range viscosity telomer oils, (i.e., sus 5000–12,000) as prepared by the procedure described in U.S. Pat. No. 5,229,023, were still plagued by problems of too high an acid number (i.e., around 50) due to cleavage of some free fatty acids during processing and pyrolysis to raise acid numbers and cause unsuitability for use of this telomer oil in products such as hydraulic fluids and gear fluids due to oxidation and corrosion associated with the free acids.

The present invention was made in an effort to improve the telomer product by lowering temperature of formation and by improving the acid number of the telomer product such that lower range viscosity telomer oil products can be used in hydraulic fluid and gear fluid formulations without causing corrosion or oxidation problems.

SUMMARY OF THE INVENTION

The present invention provides an improved lower viscosity range telomer product and an improved process for synthesizing the lower viscosity range telomer product. More specifically, the present invention provides a lower viscosity range telomer product made from a mixture of triglyceride oils wherein from about 5% to about 15% of the triglyceride oils is a conjugated triglyceride and the other triglyceride oil is an unconjugated unsaturated triglyceride, wherein the mixture of triglyceride oils that is formed into a lower viscosity range telomer by heating the mixture for from about 3 hours to about 30 hours at a temperature of from about 150° C. to about 300° C. under a non-oxidizing atmosphere (e.g., nitrogen) without a water catalyst. The conjugated triglyceride has at least 50% of the fatty acids comprising at least two conjugated double bonds. Preferably, at least 50% of the fatty acids in the conjugated triglyceride oil comprise at least three conjugated double bonds. The unconjugated unsaturated triglyceride has from about 10% to about 75% of its fatty acids being polyunsaturated and having from about 16 to about 26 carbon atom chain length (unbranched). The improved lower viscosity range telomer product is useful as an antiwear agent and as a thickening agent in compositions such as hydraulic fluids and gear fluids where low acid number is important to avoid corrosion. A lower viscosity range telomer product has a viscosity of from 5000 to 12,000 sus (kinematic viscosity) at 40° C. and an acid number lower than 20.

The present invention further provides an improved lower viscosity range telomer oil produced by a process and a process for synthesizing a lower viscosity range telomer oil, comprising heating a mixture comprising from about 5% to about 15% of a conjugated triglyceride, wherein the conjugated triglyceride has at least 50% of fatty acids polyunsaturated with at least two conjugated double bonds and from about 85% to about 95% of an unconjugated unsaturated triglyceride, wherein the unconjugated unsaturated triglyceride has from about 10% to about 75% of its fatty acids being polyunsaturated and having from about 16 to about 26 carbon atom chain length (unbranched), in a non-oxidizing atmosphere at from about 150° C. to about 300° C. for from about 3 hours to about 30 hours to lower the total number of polyunsaturated fatty acids in the conjugated triglyceride oil and vegetable triglyceride oil to less than 10% through the formation of aliphatic rings. Preferably the conjugated triglyceride comprises at least three conjugated double bonds in at least 50% of its fatty acids. Preferably, the conjugated triglyceride is heated without water, which can catalyze pyrolysis and cleavage (hydrolysis) of the fatty acids.

As a result of the lower reaction temperatures, the telomer oil products from this improved process have an improved, lighter color.

DETAILED DESCRIPTION OF THE INVENTION

Figure 1:
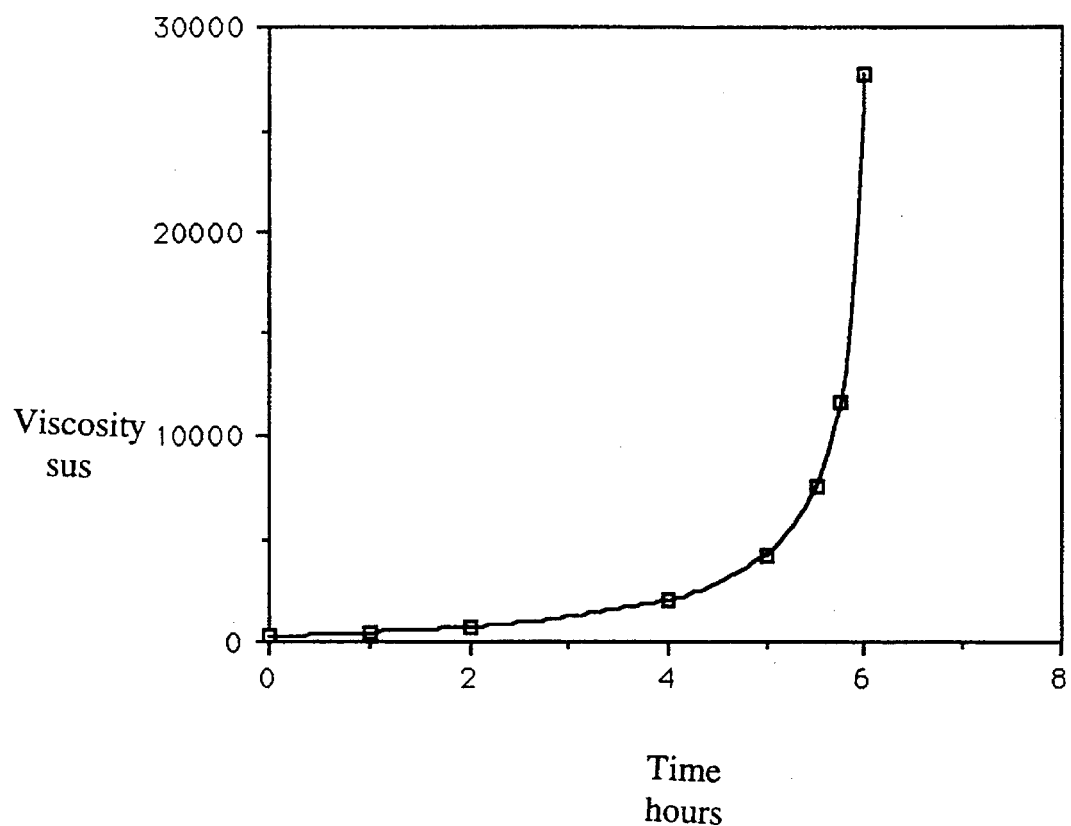
FIG. 1 shows a graph of viscosity (kinematic viscosity at 40° C. sus) versus time for a telomer synthesis run using a 50:50 mixture of rapeseed oil and tung oil (conjugated oil). The reaction could not be stopped and the product had too high a viscosity.

The present invention represents a surprising improvement over the telomer oil art and provides an improved lower viscosity range telomer oil using a process that requires a lower processing temperature and a faster reaction time than the original telomer invention described in U.S. Pat. No. 5,229,023. Another advantage of the present invention over the improved telomer oil described in U.S. Pat. No. application 08/108,477 are: (1) the other process uses higher amounts (e.g., 30–50% by weight) of more expensive conjugated oils such as tung oil, (2) conjugated oils have supply and availability problems causing the need to minimize their use, and (3) higher levels of tung oil have cause autocatalytic reactions resulting in difficulty in controlling the viscosity of the finished telomer oil product.

The present invention provides an improved lower viscosity range telomer product. More specifically, the present invention provides a lower viscosity range telomer product having a kinematic viscosity of from about 5000 sus to about 12,000 sus at 40° C. and an acid number lower than 20, preferably an acid number lower than 10. Such a lower viscosity range telomer oil product has not been made before with an acid number lower than 20. Preferably, the lower viscosity range telomer oil product is made from a mixture of triglyceride oils wherein from about 5% to about 15% of the triglyceride oils is a conjugated triglyceride and the other triglyceride oil is an unconjugated unsaturated triglyceride, wherein the mixture of triglyceride oils that is formed into a lower viscosity range telomer by heating the mixture for from about 3 hours to about 30 hours at a temperature of from about 150° C. to about 300° C. under a non-oxidizing atmosphere (e.g., nitrogen) without a water catalyst. Most preferably, the acid number is less than 10.

The present invention further provides an improved lower viscosity range telomer oil produced by a process and a process for synthesizing a lower viscosity range telomer oil, comprising heating a mixture comprising from about 5% to about 15% of a conjugated triglyceride, wherein the conjugated triglyceride has at least 50% of fatty acids polyunsaturated with at least two conjugated double bonds and from about 85% to about 95% of an unconjugated unsaturated triglyceride, wherein the unconjugated unsaturated triglyceride has from about 10% to about 75% of its fatty acids being polyunsaturated and having from about 16 to about 26 carbon atom chain length (unbranched), in a non-oxidizing atmosphere at from about 150° C. to about 300° C. for from about 3 hours to about 10 hours to lower the total number of polyunsaturated fatty acids in the conjugated triglyceride oil and vegetable triglyceride oil to less than 10% through the formation of aliphatic rings. Preferably, the conjugated triglyceride is heated without water, which can catalyze pyrolysis and cleavage (hydrolysis) of the fatty acids. The process for producing a telomer oil with an acid number less than 20 and preferably less than 10 further solves a problem of an autocatalytic reaction, making it difficult to control the viscosity of the telomer oil when higher levels(e.g., greater than 15%) of conjugated oils are used. For example, a 50:50 (by weight) mixture of rapeseed oil and tung oil was heated for 6 hours at 220° C. (under nitrogen with stirring) and had a viscosity of 27500 sus when a small sample was removed and rapidly cooled in 5 min. By the time the larger batch had cooled (in about an hour) the viscosity had increased to 35500 sus. A similar problem occurred with a batch of 67:33 (by weight) rapeseed oil:tung oil.

The conjugated triglyceride has at least 50% of the fatty acids comprise at least two conjugated double bonds. The unconjugated unsaturated triglyceride has from about 10% to about 75% of its fatty acids being polyunsaturated and having from about 16 to about 26 carbon atom chain length (unbranched). Several appropriate unconjugated unsaturated triglyceride oils were illustrated, such as those vegetable triglyceride oils selected from the group consisting of rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

The essential characteristic of the conjugated triglyceride oil is the presence of conjugated double bonds in at least 50% of the fatty acids in the triglyceride oil. Preferably, at least 50% of the fatty acids in the conjugated triglyceride oil comprise at least three conjugated double bonds. Examples of appropriate conjugated triglyceride oils include, for example, tung oil, oitcica oil, seed fats of Rosaceae, Euphorbiaceae, and Cucurbitaceae families, fish oils enriched in ω-3 fatty acids, and combinations thereof. Tung oil was used as an example of a conjugated triglyceride oil. Tung oil is made from kernels of the fruit of the tung tree, which has been grown in China for centuries and more recently (since 1925) grown in southeastern United States. The tung kernels have about a 17.5% oil content. Tung oil generally has a saponification number of 189–195, an iodine number of 160–175, an R.I. at 25° C. of 1.516–1.520 and unsaponified matter below 1%. The fatty acid profile of tung oil is shown in Table 1 below.

TABLE 1

| Fatty Acid | Percent (%) |
| --- | --- |
| oleic acid | 4–9 |
| linoleic acid | 8–10 |
| saturated | 2–6 |
| α-eleostearic acid | 77–86 |
| linolenic acid | trace |

α-Eleostearic acid is a conjugated fatty acid, such as 9,11,13-octadecatrienoic acid, and linolenic acid is predominantly (not conjugated) 9,12,15-octadecatrienoic acid. The cold water fish oils (and cod liver oil) contain high levels of the polyunsaturated fatty acids eicosapentaenoic acid and docosahexaenoic acid.

The present invention found a surprising improvement in the properties and processing characteristics lower range viscosity telomer oils that were previously made without the use of conjugated triglyceride oils in the triglyceride oil mixture. For example, a 6000 sus telomer oil (made from rapeseed oil and linseed oil, two unconjugated unsaturated triglyceride oils) was tested in several hydraulic fluid formulations. However, it did not pass any of the oxidation and corrosion tests because its acid number was too high (around 50). This created the need for lower range viscosity telomer oils with much lower acid numbers to solve the problem of corrosion in the hydraulic fluid formulations. The resulting improved lower viscosity range telomer oil has increased solubility in a variety of lubricant base oils, is lighter in color and has a lower acid number (a measure of the amount of free fatty acids present) that previous telomer oils made without a conjugated triglyceride oil. Therefore, a lower range viscosity telomer oil with an acid number of less than 20 and a viscosity range of from 5000 sus to 12,000 sus at 40 ° C. is useful to improve viscosity (thicken) and add thermal oxidative stability to hydraulic fluid and gear fluid formulations.

EXAMPLE 1

This example illustrates the problem of an autocatalytic reaction experienced when larger amounts of tung oil (i.e., conjugated oil) was used. A 50:50 (by weight) mixture of rapeseed oil:tung oil was heated for six hours at 220° C. (under nitrogen with stirring). This telomer oil had a viscosity of 27,500 sus (kinematic viscosity at 40° C. when the sample was removed from the hot oil and rapidly cooled in about 5 minutes. When the large batch of telomer oil cooled (about 1 hour later), the viscosity increased to 35,500 sus. Plotting viscosity versus time (FIG. 1) show a rapid rise of viscosity after the reaction begins, evidencing an autocatalytic effect.

Figure 2:
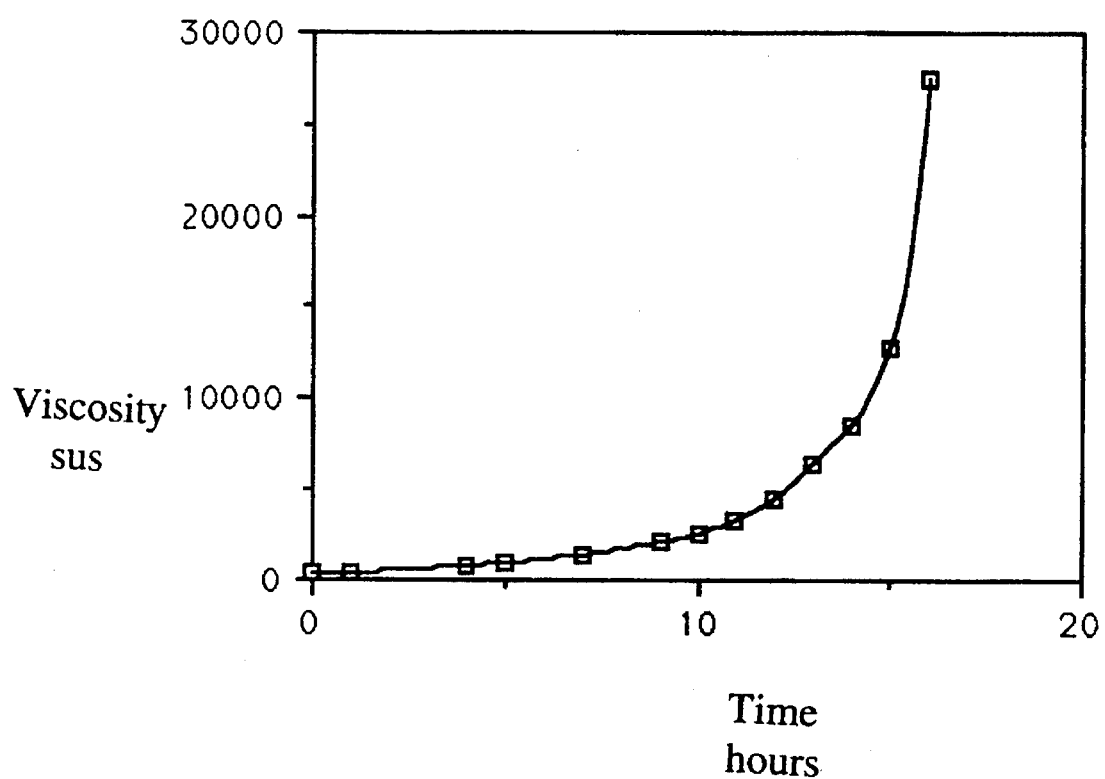
FIG. 2 shows a graph of viscosity (kinematic viscosity at 40° C. sus) versus time for a telomer synthesis run using a 67:33 mixture of rapeseed oil and tung oil (conjugated oil). The reaction could not be stopped and the product had too high a viscosity.

The autocatalytic problem was also evident when the amount of tung oil was reduced. When a 67:33 (by weight) mixture of rapeseed oil:tung oil was mixed and heated in at similar way (225° C.), a similar autocatalytic reaction was observed after about 15 hours of heating. The final product (rapidly cooled to room temperature) had a viscosity of 27,500 sus while the larger batch cooled in about 45 min. and had a final viscosity of 34,000 sus. The kinetics of this reaction are shown in FIG. 2. Therefore, these data illustrate the problem of an autocatalytic reaction that was solved by the present invention.

EXAMPLE 2

This example illustrates the development of processing parameters for synthesizing a lower viscosity range telomer oil product without an autocatalytic problem. In a 1000 ml flask, there was added with 90 g linseed oil (unconjugated unsaturated triglyceride), 90 g high erucic acid rapeseed oil (unconjugated unsaturated triglyceride) and 20 g of tung oil (conjugated triglyceride). The flask was fitted with a stirrer, thermometer, nitrogen inlet tube and air condenser. Nitrogen gas was bubbled through the mixture at room temperature for 30 min. The mixture was heated (with continuous stirring) under a steady stream of nitrogen for 24 hr. Samples (12 ml) were removed at various times to measure kinematic viscosity and acid number. The initial reaction temperature was about 260° C. for the first 5 hours of the reaction, and then it was raised to about 280° C. for the remainder of the reaction. Table 2 below shows the measurements from this sample during processing.

TABLE 2

| Time (hr) | Temp. °C. | viscosity (sus) @ 40° C. | Acid No. |
|---|---|---|---|
| 0 | 262 | 176 | 1.7 |
| 1 | 263 | 223 | |
| 3 | 260 | 297 | |
| 5 | 259 | 346 | |
| 6.1 | 283 | 434 | |
| 7.5 | 281 | 572 | |
| 8.5 | 281 | 671 | |
| 12.5 | 282 | 1036 | |
| 13.5 | 280 | 1446 | |
| 14.5 | 278 | 1783 | 4.7 |
| 16.5 | 283 | 2036 | |
| 19.5 | 280 | 2453 | 6.2 |
| 21.5 | 281 | 3305 | |
| 23.5 | 282 | 4226 | 7.7 |
| 27.5 | 283 | 5242 | 9.5 |

Figure 3:
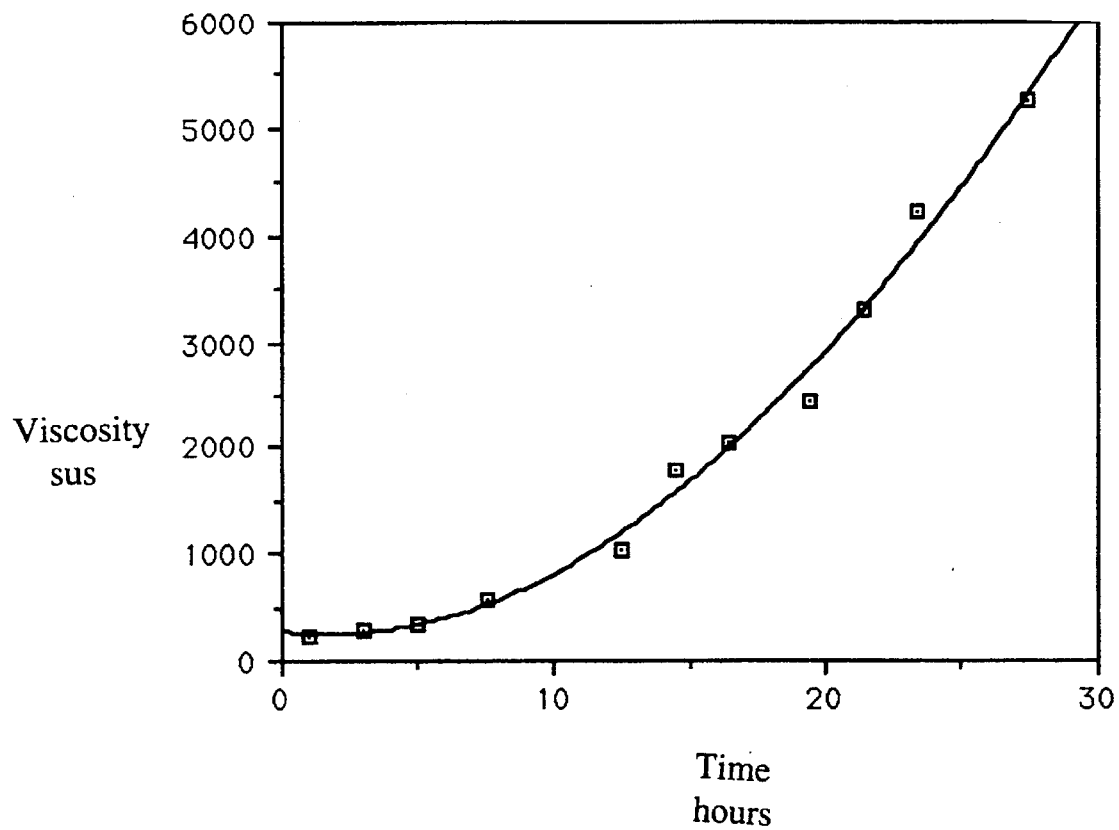
FIG. 3 shows an improvement in controlling the reaction where 10% tung oil was added to 45% linseed oil and 45% rapeseed oil (see example 2). The rise in viscosity over time was slower and the desired viscosity product could more easily achieved.

The kinetics (viscosity) of the reaction of this telomer oil is shown in FIG. 3. The reaction was stopped by slowing cooling the product to room temperature (about one hour) where there was little change in viscosity noted (from 5242 to 5280 sus). Therefore, the foregoing problem of autocatalytic processing during the cooling cycle was not in evidence.

The final product was cooled and weighed. The yield was 82 grams (plus 118 g removed for samples). The final cooled product had a kinematic viscosity of 5450 sus at 40° C. and an acid number of 10.1.

EXAMPLE 3

The procedure of example 2 was repeated except that the temperature was maintained at 290°±2° C. throughout the heating step. The volumes were doubled with 180 g high erucic acid rapeseed oil, 180 g linseed oil and 40 g tung oil. The reaction conditions are shown in Table 3 below:

TABLE 3

| Time (hr) | Temp. °C. | viscosity (sus) @ 40° C. | Acid No. |
|---|---|---|---|
| 0 | 295 | 180 | 2.2 |
| 4 | 291 | 1116 | 7.7 |
| 9 | 290 | 2230 | 9.8 |
| 12 | 291 | 3634 | |
| 16 | 291 | 5372 | 11.3 |
| 18 | 290 | 6485 | 15.1 |

Figure 4:
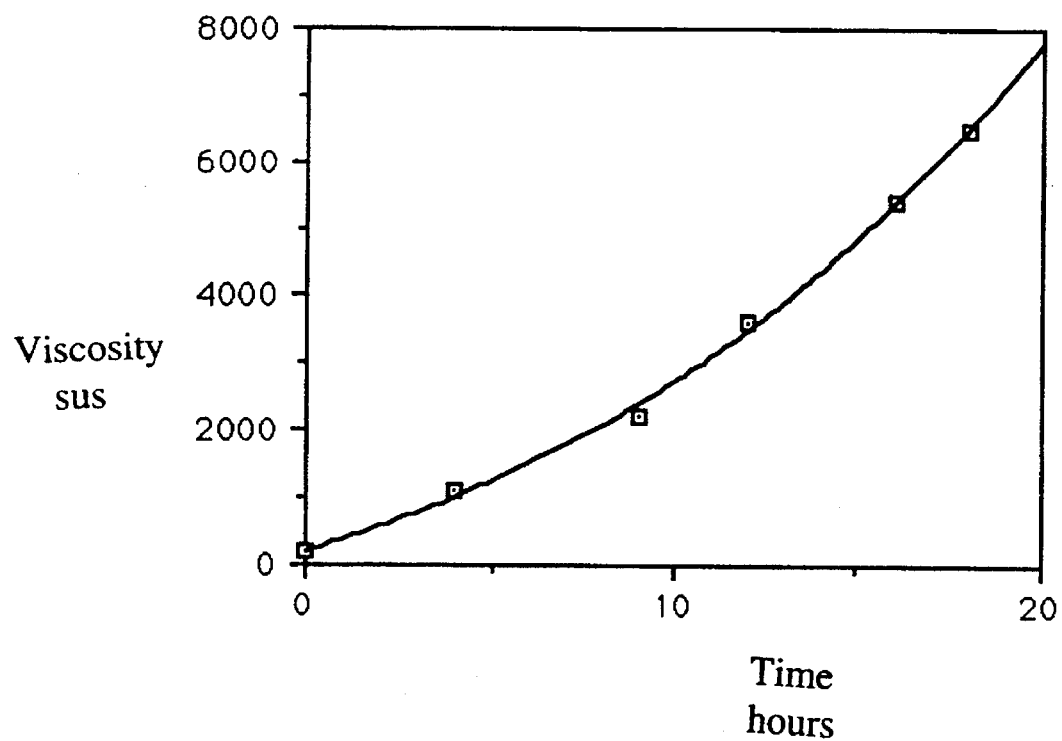
FIG. 4 shows a similar reaction reported in Table 3 in example 3. Again, 10% tung oil was used.

The kinetics (viscosity) of the reaction of this telomer oil is shown in FIG. 4. The reaction was stopped by slowing cooling the product to room temperature (about one hour) where there was little change in viscosity noted (from 6485 to 6530 sus). Therefore, the foregoing problem of autocatalytic processing during the cooling cycle was not in evidence.

I claim:

1. A lower range viscosity telomer oil with an acid number of less than 20 and a viscosity range of from about 5000 sus to about 12,000 sus at 40° C., comprising no more than 4% polyunsaturated fatty acids and a plurality of aliphatic rings, wherein the telomer oil is made from about 5% to about 15% of a conjugated triglyceride oil, wherein the conjugated triglyceride oil has at least 50% of fatty acids having at least two conjugated double bonds, and from about 85% to about 95% of an unconjugated unsaturated triglyceride oil, wherein the unconjugated unsaturated triglyceride oil has from about 10% to about 75% of its fatty acids being polyunsaturated and having from about 16 to about 26 carbon atom chain length (unbranched).

2. The lower range viscosity telomer oil product of claim 1, wherein the conjugated triglyceride oil comprises at least 50% of fatty acids having at least three conjugated double bonds.

3. The lower range viscosity telomer oil product of claim 1, wherein the conjugated triglyceride oil is tung oil, fish oils enriched in ω-3 fatty acids, cod liver oil, and combinations thereof.

4. The lower range viscosity telomer oil product of claim 3, wherein the fish oils enriched in ω-3 fatty acids are selected from the group consisting of salmon oil, herring oil, menhaden oil, sardine oil, pollack oil, other cold water fish of the north pacific, and combinations thereof.

5. The lower range viscosity telomer oil product of claim 1, wherein the unconjugated unsaturated triglyceride oil is rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

6. A lower range viscosity telomer oil produced by a process comprising heating a mixture of triglyceride oils comprising from about 5% to about 15% of a conjugated triglyceride oil, wherein the conjugated triglyceride oil has at least 50% of fatty acids polyunsaturated with at least two conjugated double bonds, and from about 85% to about 95% of an unconjugated unsaturated triglyceride oil, wherein the unconjugated unsaturated triglyceride oil has from about 10% to about 75% of its fatty acids being polyunsaturated and having from about 16 to about 26 carbon atom chain length, in a non-oxidizing atmosphere at from about 150° C. to about 300° C. for from about 3 hours to about 30 hours to lower the total number of polyunsaturated fatty acids in the conjugated triglyceride oil and the unconjugated unsaturated triglyceride oil to less than 10% through the formation of aliphatic rings and having an acid number of 20 or less.

7. The lower range viscosity telomer oil of claim 6, wherein the conjugated triglyceride oil comprises at least 50% of fatty acids having at least three conjugated double bonds.

8. The lower range viscosity telomer oil of claim 6, wherein the conjugated triglyceride oil is tung oil, fish oils enriched in ω-3 fatty acids, cod liver oil, and combinations thereof.

9. The lower range viscosity telomer oil of claim 8, wherein the fish oils enriched in ω-3 fatty acids are selected from the group consisting of salmon oil, herring oil, menhaden oil, sardine oil, pollack oil, other cold water fish of the north pacific, and combinations thereof.

10. The lower range viscosity telomer oil of claim 6, wherein the unconjugated unsaturated triglyceride oil is rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

11. A process for synthesizing a lower range viscosity telomer oil, comprising heating a mixture of triglyceride oils comprising from about 5% to about 15% of a conjugated triglyceride oil, wherein the conjugated triglyceride oil has at least 50% of fatty acids polyunsaturated with at least two conjugated double bonds, and from about 85% to about 95% of an unconjugated unsaturated triglyceride oil, wherein the unconjugated unsaturated triglyceride oil has from about 10% to about 75% of its fatty acids being polyunsaturated and having from about 16 to about 26 carbon atom chain length, in a non-oxidizing atmosphere at from about 150° C. to about 300° C. for from about 3 hours to about 30 hours to lower the amount of polyunsaturation in the conjugated triglyceride oil and unconjugated unsaturated triglyceride oil to less 4% through the formation of aliphatic rings and having an acid number of 20 or less.

12. The process of claim 11, wherein the conjugated triglyceride oil comprises at least 50% of fatty acids having at least three conjugated double bonds.

13. The process of claim 11, wherein the conjugated triglyceride oil is tung oil, fish oils enriched in ω-3 fatty acids, cod liver oil, and combinations thereof.

14. The process of claim 13, wherein the fish oils enriched in ω-3 fatty acids are selected from the group consisting of salmon oil, herring oil, menhaden oil, sardine oil, pollack oil, other cold water fish of the north pacific, and combinations thereof.

15. The process of claim 11, wherein the unconjugated unsaturated triglyceride oil is rapeseed oil, crambe oil, meadowfoam oil, soya bean oil, peanut oil, corn oil, safflower oil, sunflower seed oil, cottonseed oil, olive oil, coconut oil, palm oil, linseed oil, and combinations thereof.

* * * * *